US006632504B1

(12) United States Patent
Gillespie et al.

(10) Patent No.: US 6,632,504 B1
(45) Date of Patent: Oct. 14, 2003

(54) MULTICOMPONENT APERTURED NONWOVEN

(75) Inventors: Jay Darrell Gillespie, Simpsonville, SC (US); David D. Newkirk, Greer, SC (US); Michael M. Thomason, Simpsonville, SC (US); Gregory W. Farell, Simpsonville, SC (US); Harold E. Thomas, Greer, SC (US)

(73) Assignee: BBA Nonwovens Simpsonville, Inc., Simpsonville, SC (US)

( * ) Notice: Subject to any disclaimer, the term of this patent is extended or adjusted under 35 U.S.C. 154(b) by 0 days.

(21) Appl. No.: 09/527,864

(22) Filed: Mar. 17, 2000

(51) Int. Cl.$^7$ .............................. B32B 3/10; B32B 3/00; D04H 1/00; D04H 13/00; D04H 3/00; A61F 13/20

(52) U.S. Cl. ..................... 428/131; 428/134; 428/136; 428/147; 428/198; 428/373; 428/374; 428/395; 442/352; 442/353; 604/384

(58) Field of Search .................. 428/131, 373, 428/374, 395, 134, 136, 147, 198; 442/352, 353; 604/384

(56) References Cited

U.S. PATENT DOCUMENTS

| | | |
|---|---|---|
| 3,684,647 A | 8/1972 | Matsui et al. |
| 3,700,544 A | 10/1972 | Matsui |
| 3,725,192 A | 4/1973 | Ando et al. |
| 3,920,874 A * | 11/1975 | Dempsey et al. ........... 428/198 |
| 4,019,311 A | 4/1977 | Schippers |
| 4,051,287 A | 9/1977 | Hayashi et al. |
| 4,109,038 A | 8/1978 | Hayashi et al. |
| 4,157,419 A | 6/1979 | Mirhej |
| 4,173,678 A | 11/1979 | Hennes et al. |
| 4,233,355 A | 11/1980 | Sato et al. |
| 4,350,006 A | 9/1982 | Okamoto et al. |
| 4,460,649 A | 7/1984 | Park et al. |
| 4,517,715 A | 5/1985 | Yoshida et al. |
| 4,520,066 A | 5/1985 | Athey |
| 4,588,630 A | 5/1986 | Shimalla |
| 4,818,587 A | 4/1989 | Ejima et al. |
| 5,108,820 A | 4/1992 | Kaneko et al. |
| 5,144,729 A | 9/1992 | Austin et al. |
| 5,164,262 A | 11/1992 | Kobayashi et al. |
| 5,369,858 A | 12/1994 | Gilmore et al. |
| 5,395,693 A | 3/1995 | Cho et al. |
| 5,456,982 A | 10/1995 | Hansen et al. |
| 5,534,339 A | 7/1996 | Stokes |
| 5,549,777 A | 8/1996 | Langdon et al. |
| 5,567,501 A | 10/1996 | Srinivasan et al. |
| 5,575,874 A | 11/1996 | Griesbach, III et al. |
| 5,626,571 A | 5/1997 | Young et al. |
| 5,628,097 A | 5/1997 | Benson et al. |
| 5,633,082 A | 5/1997 | Berger |
| 5,643,240 A | 7/1997 | Jackson et al. |
| 5,656,119 A | 8/1997 | Srinivasan et al. |
| 5,658,639 A | 8/1997 | Curro et al. |
| 5,669,798 A | 9/1997 | Koczab |
| 5,688,582 A | 11/1997 | Nagaoka et al. |
| 5,804,286 A | 9/1998 | Quantrille et al. |
| 5,858,504 A | 1/1999 | Fitting |
| 5,997,989 A * | 12/1999 | Gessner et al. ............. 428/152 |

FOREIGN PATENT DOCUMENTS

| | | |
|---|---|---|
| EP | 841 156 A1 | 5/1998 |
| WO | WO 96/16216 | 5/1996 |
| WO | WO 00/28122 | 5/2000 |

* cited by examiner

*Primary Examiner*—Harold Pyon
*Assistant Examiner*—Patricia L. Nordmeyer
(74) *Attorney, Agent, or Firm*—Alston & Bird LLP

(57) ABSTRACT

A nonwoven web is provided which can be readily converted to an apertured web by stretching. In its initial non-apertured state, the web comprises a plurality of multicomponent fibers comprising at least two thermoplastic polymer components arranged in at least first and second separate continuous structured domains. The polymer component of the first domain comprises polyethylene. Prior to stretch aperturing, the web has a peak elongation of at least 100 percent and is characterized by having a plurality of discrete, spaced-apart, frangible bond sites of polymer bonding the fibers to form a coherent extensible nonwoven web. The frangible bond sites are structured and arranged to readily rupture when subjected to tensile stress to form discrete, spaced-apart apertures in the nonwoven fabric. The web has a total energy absorption in at least one of the machine direction or the cross-machine direction of at least 50 gcm/cm2.

45 Claims, 5 Drawing Sheets

MULTICOMPONENT APERTURED NONWOVEN

FIELD OF THE INVENTION

This invention relates to nonwoven webs prepared from thermoplastic polymers and to products incorporating apertured nonwoven webs.

BACKGROUND OF THE INVENTION

Apertured nonwoven webs of thermoplastic polymers are often used in the manufacture of disposable absorbent articles, including wipes, garments, and hygiene products. One typical use is as a topsheet in diapers, feminine hygiene products, incontinence garments, and the like. The topsheet is provided as a surface layer on these articles that is intended to be placed against the wearer's skin. Body fluids pass through the apertures in the topsheet into the fluid management and retention layers below.

The topsheet desirably should have a number of properties. Fluids should be rapidly drawn away from the surface of the skin and the skin should be kept dry thereafter and these properties should remain at high levels after multiple insults. The topsheet layer should be pliable, soft, and cloth-like in appearance and touch. The topsheet should also be sufficiently strong to withstand rough-and-tumble wear by the physically active without binding, tearing, or producing excessive lint or broken filaments extending from the surface of the web.

Beyond the desirable properties of the topsheet, the nonwoven web from which the topsheet or other component of a disposable absorbent article is prepared should be sufficiently strong to withstand aperturing and other processing steps. Several of the desirable properties of various nonwoven webs that make good topsheet candidates are somewhat in conflict and are difficult to balance in a single nonwoven web. For example, softer webs made from polyethylene may not be producible at commercially significant rates and may shred during aperturing. The cost of polyethylene is a factor limiting its use. Nonwoven webs used as a topsheet typically have been prepared from lower cost polypropylene, which has a high speed production rate, but produces a web that may be less soft than is desirable and aperturing can result in a higher percentage than desired of broken filaments.

Aperturing can be accomplished by a number of methods, including thermal, mechanical, and hydraulic methods known in the art. Benson et al. U.S. Pat. No. 5,628,097 describes a method for aperturing a nonwoven web by mechanical stretching. A nonwoven web is said to be weakened along a plurality of locations and then incrementally stretched to cause the web to rupture at the weakened locations. A plurality of apertures is created in the nonwoven web coincident with the weakened locations. The weakened locations are created by a roller arrangement that includes a patterned calender roll and a smooth anvil roll. One or both rolls may be heated and the pressure can be adjusted to concurrently weaken and melt-stabilize the web at a plurality of locations. The web is incrementally stretched after passing through the weakening roller arrangement by being passed through a nip formed by an incremental stretching system that uses opposed pressure applicators having complimentary three-dimensional surfaces.

It would be desirable to improve the properties of nonwoven webs for aperturing and to produce webs at high production rates having a better balance of properties for aperturing and for use as topsheet or other apertured components in the construction of disposable absorbent articles.

SUMMARY OF THE INVENTION

The invention provides apertured nonwoven webs suitable for use in disposable absorbent products that have an excellent balance of properties that are desirable for aperturing a nonwoven web and properties that are desirable in components of disposable absorbent articles. The apertured webs of the invention have a high proportion of open area and a combination of softness, high strength, low linting, and cloth-like tactile properties that have previously been unrecognized and unavailable. Elongation, bondability, softness, and machine and cross-direction tensile can be achieved at previously unattained levels.

According to one aspect of the present invention, a nonwoven web is provided which can be readily converted to an apertured web by stretching. The web comprises a plurality of multicomponent fibers comprising at least two thermoplastic polymer components arranged in at least first and second separate continuous structured domains. The polymer component of the first domain comprises polyethylene. Prior to stretch aperturing, the web has a peak elongation of at least 100 percent and is characterized by having a plurality of discrete, spaced-apart, frangible bond sites of polymer bonding the fibers to form a coherent extensible nonwoven web. The frangible bond sites are structured and arranged to readily rupture when subjected to tensile stress to form discrete, spaced-apart apertures in the nonwoven fabric.

The discrete, spaced-apart frangible bond sites can be created in the nonwoven web by applying heat and/or pressure or thermo-mechanical energy (e.g. ultrasonic energy) to the web in discrete areas. For example, the web may be passed through a heated calender nip in which one or both rolls has a patterned surface. The application of mechanical, thermal or thermo-mechanical energy deforms the fibers in the web so that the fibers begin to flow together and bond. During this process, the fibers may completely melt so as to be no longer identifiable. Alternatively, one of the structured domains (e.g. the lower-melting polyethylene) may be deformed so that it adheres to the structured domain of an adjacent fiber, while the other (higher-melting) structured domain of the fiber remains substantially intact to provide strength. This process produces frangible bond sites, which are bonded or fused areas of polymer of predetermined geometry. These frangible bond sites are elongated in shape and have an aspect ratio of at least 3:1.

The web can be mechanically stretched by various conventional methods, such as by passing the web through a nip formed by a pair of incremental stretching rollers having a plurality of teeth and a plurality of grooves or by passing the web over a spreader bar, over a bow roll, or through a tenter frame. When the web is mechanically stretched, it is believed that the frangible bond sites become areas of stress concentration within the web. Tensile stress on the web is communicated to the bond sites. Upon application of sufficient tensile stress, concentrated at the bond sites, the frangible bond sites rupture and apertures are formed coincident with the bond sites.

The first polymer domain, which contains polyethylene, is typically a lower melting point, lower modulus polymer component, should provide at least about 20 to 90 percent by weight of the multicomponent fiber. Aperturing the web tends to produce remnants of the bond site polymer at the edges of the apertures. These edge areas tend to become more pronounced and visible as the concentration of the lower modulus polymer is increased. These regions are believed to improve the integrity of the nonwoven web and one of the benefits of the invention is that these regions are not hard and rigid, but are soft.

A specific example of the invention is a stretch apertured nonwoven web of bicomponent continuous spunbond filaments in which these filaments have a sheath of polyethylene and a core of polypropylene in which the sheath comprises at least 20 percent by weight of the filaments and the core is concentric with the sheath.

Thus, a mechanically stretched apertured nonwoven suitable for use as topsheet or in wipes and the like is provided by the invention that has an excellent balance of properties for withstanding the rigors of mechanical stretching and aperturing and also has a balance of softness, strength and other properties desirable in disposable absorbent articles.

Figure 1:
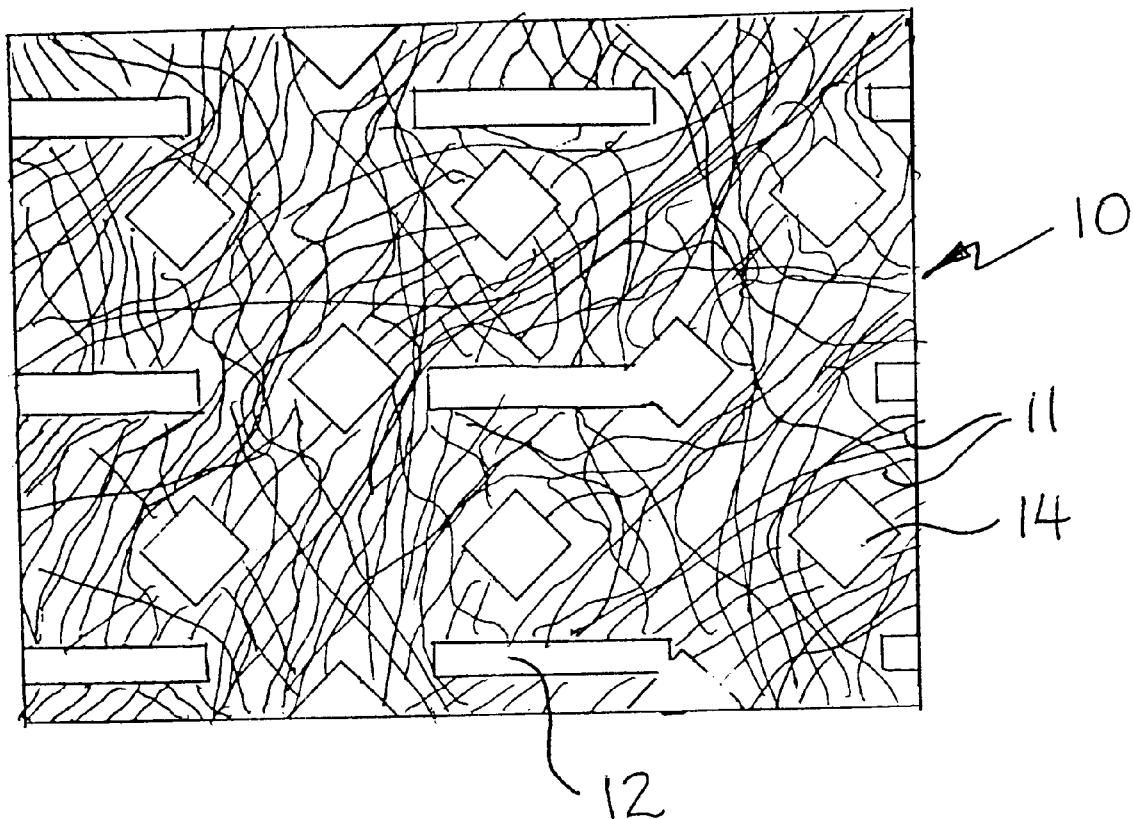
FIG. 1 is schematic illustration of a nonwoven web in accordance with the present invention prior to being stretch apertured.

The present invention will be described more fully hereinafter in connection with illustrative embodiments of the invention which are given so that the present disclosure will be thorough and complete and will fully convey the scope of the invention to those skilled in the art. However, it is to be understood that this invention may be embodied in many different forms and should not be construed as being limited to the specific embodiments described and illustrated herein. Although specific terms are used in the following description, these terms are merely for purposes of illustration and are not intended to define or limit the scope of the invention.

DETAILED DESCRIPTION OF ILLUSTRATIVE EMBODIMENTS

As used herein, the terms "nonwoven web" and "nonwoven fabric" refer to a web structure formed of individual fibers, filaments, strands or threads which are interlaid in a generally random arrangement, in contrast to a woven fabric where individual strands are interwoven in an identifiable repeating manner. Nonwoven webs may be formed by a variety of processes such as meltblowing, spunbonding, film aperturing, and staple fiber carding. Preferably, the nonwoven web of the present invention is made with continuous spunbond multicomponent filaments which are extruded, drawn, and laid on a traveling forming surface in accordance with well known spunbonding technology.

As used herein, the term "spunbond filaments" refers to small diameter substantially continuous filamentary strands which are formed by extruding a molten thermoplastic material as filaments from a plurality of fine capillaries of a spinneret with the extruded filaments then drawn and attenuated by eductive drawing or other well-known spunbonding mechanisms.

As used herein, the term "meltblown fibers" refers to fibers formed by extruding a molten thermoplastic material through a plurality of fine die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers. As used herein, the term "microfibers" refers to small diameter fibers having an average diameter not greater than about 15 microns.

As used herein, the term "polymer" generally includes, but is not limited to, hompolymers, copolymers, such as, for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiaotactic and random symmetries. The term blend is also used generally herein, and is intended to include immiscible and miscible polymer blends. The polymers are considered to be "immiscible" if they exist in separate, distinct phases in the molten state; all other blends are considered to be "miscible." It is understood that varying levels of miscibility can exist, and are also intended to be within the scope of this invention.

The term "fiber" includes fibers of indefinite length (filaments) and fibers of discrete length, such as staple fibers. The term "multicomponent fiber" refers to a fiber having at least two distinct longitudinally coextensive structured polymer domains in the fiber cross-section, as opposed to blends where the domains tend to be dispersed, random or unstructured. The distinct domains may thus be formed of polymers from different polymer classes (e.g., nylon and polypropylene) or be formed of polymers from the same polymer class (e.g., nylon) but which differ in their properties or characteristics. The term "multicomponent fiber" is thus intended to include concentric and eccentric sheath-core fiber structures, symmetric and asymmetric side-by-side fiber structures, island-in-sea fiber structures, pie wedge fiber structures, and hollow fibers of these configurations.

In FIG. 1, reference character 10 generally indicates a nonwoven web in accordance with the invention prior to being apertured. The nonwoven web includes a plurality of multicomponent fibers 11 and may be made by any of a number of manufacturing techniques well known in the nonwovens field, such as but not limited to carding, spunbonding, wet laying, air laying, meltblowing, and the like. In the particular embodiment illustrated in FIG. 1, the nonwoven fibrous web 10 is a spunbonded nonwoven comprising multicomponent spunbond continuous filaments. The spunbonded web may be produced by the conventional spunbond process wherein molten polymer is extruded into continuous filaments which are subsequently quenched, attenuated by a high velocity fluid and collected in random arrangement on a collecting surface. After filament collection, any thermal, chemical or mechanical bonding treatment may be used to form a bonded web such that a coherent web structure results.

In the embodiment shown in FIG. 1, web 10 is bonded by a two sets of intermittent discrete bond sites, indicated generally at 12 and 14, distributed throughout the web to form a unitary, coherent nonwoven structure. The bonds are preferably produced by thermal or ultrasonic point bonding using one or more cylindrical calender rolls having a desired pattern of raised points or projections. Preferably the bond sites 12 and 14 cover between 10 and 60 percent of the area of the web 10, more preferably 12 to 40 percent and most preferably 12 to 36 percent. By bonding the web in accordance with these percentage ranges, the filaments are allowed to elongate throughout the full extent of stretching while maintaining the strength and integrity of the web.

It will be seen that the two sets of bond sites 12 and 14 are of distinctly different shape or geometry. The bond sites 12 of the first set are structured and arranged to readily rupture when subjected to tensile stress to form discrete, spaced-apart apertures in the nonwoven web. These readily ruptured, frangible bond sites 12 are elongated in shape, and the polymer material from the fibers of the web has been compressed and caused to flow into a thin, brittle polymer mass. Preferably, the elongated frangible bond sites 12 have an aspect ratio of at least 3:1, more preferably at least 4:1, and most desirably at least about 5:1. As used herein, the "aspect ratio" is the ratio of the maximum length of the bond site to its maximum width. In the embodiment shown, the frangible bond sites 12 have the shape of an elongate narrow rectangle and they are oriented parallel to the machine direction of the web so that aperturing can be accomplished by stretching the web in the cross-machine direction using conventional stretching methods, such as ring rolling. However, the webs of the present invention may be designed to be apertured by stretching in either the machine direction (MD) or the cross-machine direction (CD). Typically, the elongate frangible bond sites 12 should be oriented on the web with the longest dimension extending perpendicular to the desired direction of stretching. Thus, for example, for a web which is to be stretched by CD ring-rolling, the bond sites will be oriented extending in the MD. The specific size and spacing of the frangible bond sites 12 may be varied as desired in order to obtain apertures of the desired spacing and open area, depending upon the particular properties desired. Typically, the frangible bond sites 12 may have an overall maximum length of from 1 to 8 mm, an overall maximum width of from 0.1 to 1 mm and may form a bond area of from 5 to 30 percent of the overall area of the non-apertured web.

If desired, the web 10 may be produced with only the frangible bond sites 12. However, for enhanced web physical properties, fiber tie-down and appearance, the web is suitably produced with a second set bond sites 14 which are structured and arranged to retain their integrity when the web is subjected to tensile stress during stretch aperturing. The second set of bond sites 14 may be produced separately from the first set 12 by directing by the web through a calender having the desired pattern of raised points or projections. In this case, the bond sites 14 of the second set may, in some instances, overlie the frangible bond sites 12 in certain areas, but a significant proportion of the sites 14 will be present at locations between the frangible bond sites 12. Alternatively, if desired, both sets of bond sites may be produced simultaneously using an appropriately patterned calender roll. The non-frangible bond sites 14 suitably have a generally non-elogated configuration with an aspect ratio of no more than 2:1. Conventional point bond configurations, such as diamond-shape or circular, may be used. Preferably these bonds have an overall maximum width and length of from about 0.25 mm to about 2 mm and may have a bond area of about 5 to about 30 percent of the non-apertured web.

In order to be susceptible to stretch aperturing, the web 10 is manufactured to have relatively high elongation properties. More particularly, the multicomponent fibers which are used in producing the web are engineered to impart to the web the ability to be elongated readily under relatively low tensile loads. Preferably, the nonwoven web, prior to aperturing or other mechanical treatment, has a peak elongation of at least 100 percent. Preferably, for aperturing by ring rolling at commercially desirable speeds, the web should have a peak elongation of at least 200 percent. The web in this non-apertured state has a minimum cross-machine direction tensile strength of 300 grams. Tensile strength and peak elongation are measured generally following ASTM D1682-64. Because the web is highly elongatable and readily apertures upon application of tensile stress, the tension force exerted by the tensile testing instrument may produce apertures in the sample before the peak tensile load is reached.

Figure 2:
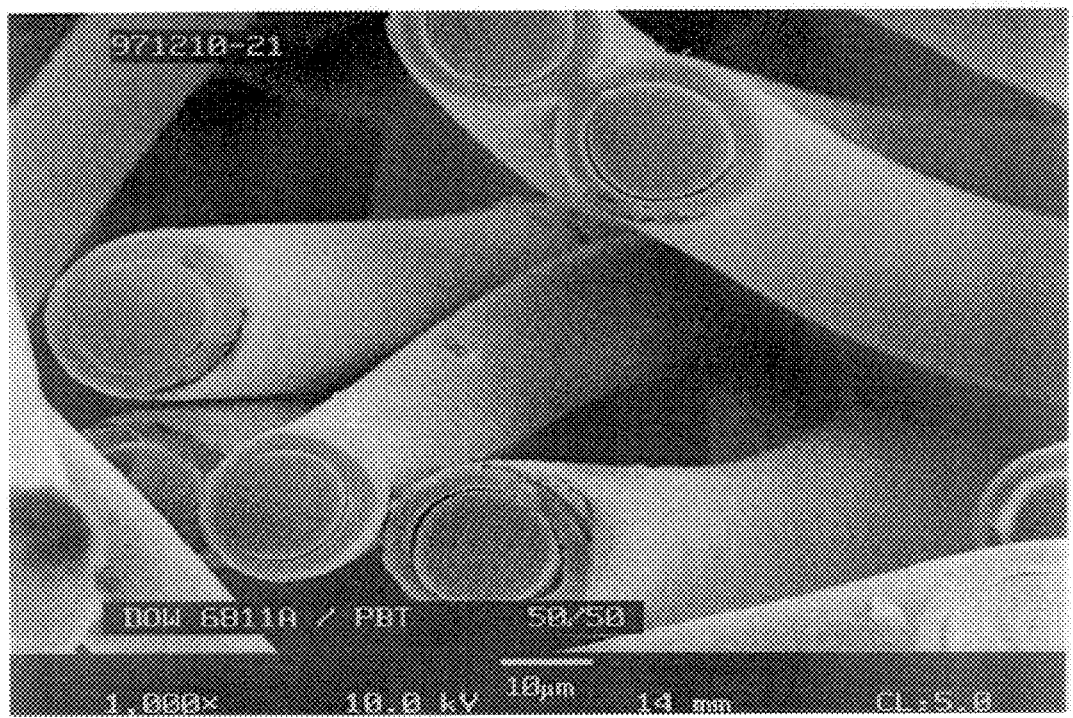
FIG. 2 is a photomicrograph of a bicomponent fiber used in the nonwoven web.

Turning to FIG. 2, an exemplary multicomponent fiber of the invention is illustrated. As illustrated in FIG. 2, in a preferred embodiment of the invention, the fibers are bicomponent fibers having an inner core polymer domain and surrounding sheath polymer domain. For purposes of illustration only, the present invention will generally be described in terms of a bicomponent fiber comprising two components. However, it should be understood that the scope of the present invention is meant to include fibers with two or more structured components.

The cross section of the multicomponent fiber is preferably circular, since the equipment typically used in the production of multicomponent synthetic fibers normally produces fibers with a substantially circular cross section. In general, the polymer domains or components are arranged in substantially constantly positioned distinct zones across the cross section of the multicomponent fiber and extend continuously along the length of the multicomponent fiber. The configuration of the first and second components in a fiber of circular cross section can be either concentric or acentric, the latter configuration sometimes being known as a "modified side-by-side" or an "eccentric" multicomponent fiber. A preferred configuration is a sheath/core arrangement, wherein a first component, the sheath, substantially surrounds a second component, the core. The weight ratio of polymer domains or components can vary. Typically, the first polymer component comprises about 20 to 90 percent by weight of the fiber and the second polymer component comprises about 10 to 60 percent by weight of the fiber. Other structured fiber configurations as known in the art may be used, such as side-by-side, segmented pie, islands-in-the-sea, or tipped multilobal structures, or hollow versions of these configurations.

The first polymer component preferably is a relatively low modulus polymer which contributes good softness to the fiber and the resulting nonwoven web. Polyethylene is particularly suited for this purpose, and it therefore preferred that the polymer component of one of the polymer domains includes polyethylene. The polymer component may be formed entirely of one or more polyethylene polymers or may be a blend of polyethylene with one or more other polymers. As used herein, "polyethylene" or "polyethylene polymer" is intended to include polyethylene homopolymers, copolymers, terpolymers and blends, including for example, low density polyethylene, medium density polyethylene, linear low density polyethylene or high density polyethylene, as well as heterophasic polyethylene compositions such as may be produced using metallocene catalysts. As an example, a branched (i.e., non-linear)

low density polyethylene or a linear low density polyethylene (LLDPE) can be utilized and produced from any of the well known processes, including metallocene and Ziegler-Natta catalyst systems. LLDPE is typically produced by a catalytic solution or fluid bed process under conditions established in the art. The resulting polymers are characterized by an essentially linear backbone. Density is controlled by the level of comonomer incorporated into the otherwise linear polymer backbone. Various alpha-olefins are typically copolymerized with ethylene in producing LLDPE. The alpha-olefins which preferably have four to eight carbon atoms, are present in the polymer in an amount up to about 10 percent by weight. The most typical comonomers are butene, hexene, 4-methyl-1-pentene, and octene. In general, LLDPE can be produced such that various density and melt index properties are obtained which make the polymer well suited for melt-spinning with polypropylene. In particular, preferred density values range from 0.87 to 0.95 g/cc (ASTM D-792) and melt index values usually range from 0.1 to about 150 g/10 min. (ASTM D1238-89, 190° C.). Preferably, the LLDPE should have a melt index of greater than 10, and more preferably 15 or greater for spunbonded filaments. Particularly preferred are LLDPE polymers having a density of 0.90 to 0.945 g/cc and a melt index of greater than 25. Examples of suitable commercially available linear low density polyethylene polymers include those available from Dow Chemical Company, such as ASPUN Type 6811 (27 MI, density 0.923), Dow LLDPE 2500 (55 MI, 0.923 density), Dow LLDPE Type 6808A (36 MI, 0.940 density), and the Exact series of linear low density polyethylene polymers from Exxon Chemical Company, such as Exact 2003. Other polyethylenes useful for this invention are available from Huntsman, Inc. and Nova Chemical.

The second polymer component may comprise any of a variety of fiber-forming synthetic polymers which may be meltspun as a multicomponent fiber with the first polymer component. Particularly suitable are polyesters, including polyethylene terephthalate and polybutylene terephthalate, polyolefins such as polypropylene, and polyamides. Various polypropylenes made by processes known to the skilled artisan may also be employed. In general, the polypropylene component can be an isotactic or syndiotactic propylene homopolymer, copolymer, or terpolymer. Examples of commercially available propylene homopolymers which can be used in the present invention include HIMONT Grade X10054-12-1 (65 MFR), Exxon Type 3445 (35 MFR), Exxon Type 3635 (35 MFR) AMOCO Type 10-7956F and 7957, and Aristech CP 350 J (melt flow rate approximately 35). Examples of commercially available copolymers of propylene include Exxon 9355 which is a random propylene copolymer with 3% ethylene, 35 melt flow rate; Rexene 13S10A, a 10 melt flow rate random propylene copolymer with 3% ethylene; Fina 7525MZ, an 11 melt flow rate 3% ethylene random propylene copolymer; Montel EPIX 30F, a 1.7% ethylene, 8 melt flow rate random copolymer of propylene and co- and ter-polymers of propylene from the Catalloy™ series from Himont.

Preferred polyamides useful to form the multicomponent fibers of this invention are those which are generically known by the term "nylon" and are long chain synthetic polymers containing amide (—CO—NH—) linkages along the main polymer chain. Suitable melt spinnable, fiber-forming polyamides include those which are obtained by the polymerization of a lactam or an amino add, or those polymers formed by the condensation of a diamine and a dicarboxylic acid. Typical polyamides useful in the present invention include nylon 6, nylon 6/6, nylon 6/9, nylon 6/10, nylon 6T, nylon 6/12, nylon 11, nylon 12, nylon 4,6 and copolymers thereof or mixtures thereof. Polyamides can also be copolymers of nylon 6 or nylon 6/6 and a nylon salt obtained by reacting a dicarboxylic acid component such as terephthalic acid, isophthalic acid, adipic acid or sebacic acid with a diamine such as hexamethylene diamine, methaxylene diamine, or 1,4bisaminomethylcyclohexane. Preferred are poly-caprolactam (nylon 6) and polyhexamethylene adipamide (nylon 6/6). Also biodegradable polymers such as PLA (polylactic acid) or PVA (polyvinyl alcohol) may be used.

In another aspect of the invention, at least one polymer domain is formed of a polymer blend, as described in more detail below. Other of the polymer domains of the fibers of the invention can be formed of a single polymer or of a polymer blend, including but not limited to any of the polymer blends described below. Advantageously, at least one polymer domain or component comprising the polymer blend forms an exposed surface on at least a portion of the fiber. The polymers of the blend can be miscible, immiscible, or a combination of miscible and immiscible polymers. In one embodiment, the polymers may exist as a dominant continuous phase and at least one substantially discontinuous dispersed phase. In the case where the blend exists as a dominant continuous phase and at least one discontinuous phase, other polymers may also be present which are either miscible in one, or the other, or both polymer phases.

For example, according to one embodiment, the first polymer domain of the multicomponent fibers may comprise between 2 to 50 percent by weight of a propylene polymer, e.g. a 3% ethylene-propylene copolymer, and 98 to 50 percent by weight polyethylene. In one particular embodiment, at least one polymer domain of the multicomponent fiber may range from 5 to 40 percent by weight propylene polymer, and most desirably between 5 to 25 percent by weight propylene polymer and 75 to 95 percent by weight polyethylene. For example, the polymer domain may contains 5 to 25 percent by weight of ethylene-propylene copolymer or terpolymer and 75 to 95 percent by weight linear low density polyethylene. In these embodiments, the lower melting polyethylene is present as a substantially continuous phase in the blend and the higher melting propylene polymer is present as a discontinuous phase dispersed in the polyethylene phase. When the lower-melting polyethylene component is present as a substantially continuous phase and the higher-melting polypropylene is present as a discontinuous phase dispersed in the polyethylene phase, the lower-melting polyethylene component and the higher-melting polypropylene component can be present in proportions ranging from about 50 to about 99 percent by weight polyethylene and about 50 to about 1 percent polypropylene, more preferably from about 50 to about 98 percent by weight polyethylene and about 50 to about 2 percent polypropylene, more preferably from about 60 to about 95 percent by weight polyethylene and about 40 to about 5 percent polypropylene, and most preferably from about 75 to about 95 percent by weight polyethylene and about 25 to about 5 percent polypropylene.

In another aspect of the invention, the second polymer domain may be formed of a polymer blend. For example, the second polymer domain may include a dominant amount of a propylene polymer, such as isotactic polypropylene, a small amount of a polymer having low mutual affinity with the dominant polymer, such as polyethylene, and an additional third polymer which either reduces crystallinity and/or compatibilizes the blend. Preferred multicomponent fibers according to this embodiment may comprise greater than 50 percent by weight propylene polymer, 1 to 10 percent polyethylene, and 10 to 40 percent of the third polymer. Suitable additional third polymers include propylene copolymers and terpolymers such as the commercially available Catalloy.TM. copolymers available from Montell. These resins are characterized by having the comonomer(s) exist to some degree in blocks, and wherein at least some portion of the polymer chain is miscible with one or the other, or both, dominant and dispersed polymer phases. Other suitable polymers are the Reflex.TM. flexible polyolefins from Rexene. These crystallinity reducing resins are characterized as having atactic segments present in the polymer chain, such that the "tacticity" of the polymer is affected. Especially preferred multicomponent fibers according to this embodiment comprise 65 to 80 percent isotactic polypropylene, 1 to 5 percent polyethylene, and 15 to 30 percent of a polyolefin copolymer wherein at least a portion of the chain is miscible with isotactic polypropylene.

Since the polymers employed in the invention will undergo extrusion, stabilizers and antioxidants are conventionally added to the polymer. Other additives may also be added in accordance with the present invention. For example inorganic additives such as titanium dioxide, talc, fumed silica or carbon black may be included. The polymer resin may also contain other additives, such as other polymers, diluents, compatibilizers, antiblocking agents, impact modifiers, plasticizers, UV stabilizers, pigments, delusterants, lubricants, wetting agents, antistatic agents, nucleating agents, rheology modifiers, water and alcohol repellents, and the like. It is also anticipated that additive materials which have an affect on processing or product properties, such as extrusion, quenching, drawing, laydown, static and/or electrical properties, bonding, wetting properties or repellency properties may also be used in combination with the blend. In particular, polymeric additives may also be used that impart specific benefits to either processing and/or end use. For certain topsheet applications it may be important to increase the hydrophilicity of the web. This may be accomplished by incorporating appropriate additives into the polymer melt of the sheath component or by topically applying a surfactant additive to the web by foam or other known coating techniques.

Apertures are produced in the web by stretching the web 10. Preferably, the web is stretched in a direction transverse to the orientation of the elongated bond sites 12. Numerous established techniques can be employed in carrying out this operation. For example, a common way for obtaining MD elongation is to pass the web through two or more sets of nip rolls, each set moving faster than the previous set. CD elongation may be achieved through tentering. Other means maybe employed; for example, "ring rolling" as disclosed in U.S. Pat. 5,242,436 to Weil et al., incorporated herein by reference, is often used in obtaining CD and/or MD elongation.

Upon application of elongation forces on web, fibers oriented in the direction of the elongation experience tension and undergo deformation. During this process, the fibers are capable of elongating well beyond their unstretched length. However, tensile forces concentrated in the frangible bond sites 12 cause the bond sites to rupture and form clearly defined apertures. The intermittent non-frangible bond sites distributed throughout the web are of high strength and maintain their integrity such that fibers are sufficiently tied down. Accordingly, fiber detachment is reduced with the desirable result that abrasion resistance is maintained and fuzzing is minimized. Moreover, web strength is maintained as the coherent web structure is kept intact during the elongation operation.

The basis weight of the apertured web may typically range from about 10 to about 40 grams per square meter (gsm) for most hygiene applications, and higher for other end use applications. The basis weight of the apertured web is dictated by the basis weight of the unstretched web and the extent of stretching performed during aperturing.

In one particularly suitable embodiment of the present invention, the web can be produced as a laminate of two or more webs of lighter basis weight. For example, in an in-line manufacturing operation, a first web may be deposited on a moving belt and then two or more additional webs can be successively deposited, after which the web layers can be bonded by passing through one or more calender stacks. It is also possible to produce two or more separate webs by conventional methods, each bonded with a pattern of non-frangible bond sites 14, with the webs then being combined and bonded to one another by a calender roll which produces the desired configuration of frangible bond sites 12. According to this aspect of the invention, an apertured web can be produced with different properties or characteristics on opposite sides. For example, a first web having a first bicomponent fiber composition (e.g. 50% PE, 50% PP) may be combined with a second web having a different bicomponent fiber composition (e.g. 80% PE, 20% PP). One surface has a higher content of the softer polyethylene, for aesthetic purposes, while the other surface has a higher content of the higher modulus polypropylene for to impart desired physical and mechanical properties.

The apertured nonwoven web of the present invention have excellent tensile strength and toughness. Total tensile energy absorption (TEA) is a tensile measurement which is representative of web toughness. Apertured webs in accordance with the present invention have TEA of at least 50 gcm/cm$^2$ in at least one of the machine direction (MD) or the cross-machine direction (CD), and more preferably they typically have a greater than 100 gcm/cm$^2$. Preferred webs in accordance with the invention have a TEA in both the MD and CD of at least 100 gcm/cm2, and a strip tensile strength in at least one of the machine direction or the cross-machine direction of at least 300 g. Apertured webs of the invention exhibit excellent strip tensile strength and TEA in both the direction of stretch aperturing and in a direction transverse thereto.

The apertured webs of the present invention are useful in numerous applications. In addition to uses as a topsheet component or as a wipe, as previously noted, the webs may be used as other components in absorbent products, such as a backsheet fabric, an acquisition-distribution layer, or as a waistband. Other uses include disposable garments, bedding and home furnishings, interlining material, filter media, as a flexible classification screen, in packaging, and bandages.

The following non-limiting examples are given to further illustrate the invention.

EXAMPLE 1

A nonwoven web having a basis weight of 60 gsm was prepared in accordance with the invention from continuous spunbond bicomponent filaments. The continuous filaments had a sheath and core configuration in which the core was concentric within the sheath. The sheath was prepared from a composition in which the fiber spinning polymer was 100 percent polyethylene obtained from Dow Chemical Company and designated by Dow as PE 6811-A. The core was prepared from a composition in which the fiber spinning polymer was 100 percent polypropylene obtained from Amoco Oil Corporation and designated by Amoco as 7957 PP.

The spunbond web was bonded by the application of heat and pressure by passing the web through a calender nip between a heated, patterned calender roll and a smooth anvil roll. The patterned calender roll produced a diamond-shaped pattern of discrete, spaced apart, non-frangible bond sites of polymer. These non-frangible bond sites are structured and arranged to maintain their integrity when subjected to tensile stress and to impart strength and integrity to the web. The aspect ratio of these diamond-shaped bond sites is approximately 1:1 and they are approximately 1 mm in the longest dimension.

The web was then bonded a second time to produce a plurality of discrete, spaced-apart frangible bond sites of polymer. The frangible bond sites were produced in a manner similar to the production of the non-frangible bond sites. However, the bonding patterns that are produced for the frangible bond sites are elongated in shape in the machine direction and have an aspect ratio of approximately 5:1. These rectangular bonds are structured and arranged to readily rupture when subjected to cross-direction tensile stress to form discrete, spaced-apart apertures.

After the frangible bond sites were produced, the web was subjected to tensile stress, primarily in the cross-machine direction, by mechanical stretching in accordance with the procedure set forth in Benson et al. U.S. Pat. No. 5,628,097, the contents of which are incorporated herein by reference. The frangible bond sites readily ruptured, while the non-frangible bond sites maintained the integrity of the web. The resulting web had a basis weight of approximately 37 grams per square meter.

Figure 3:
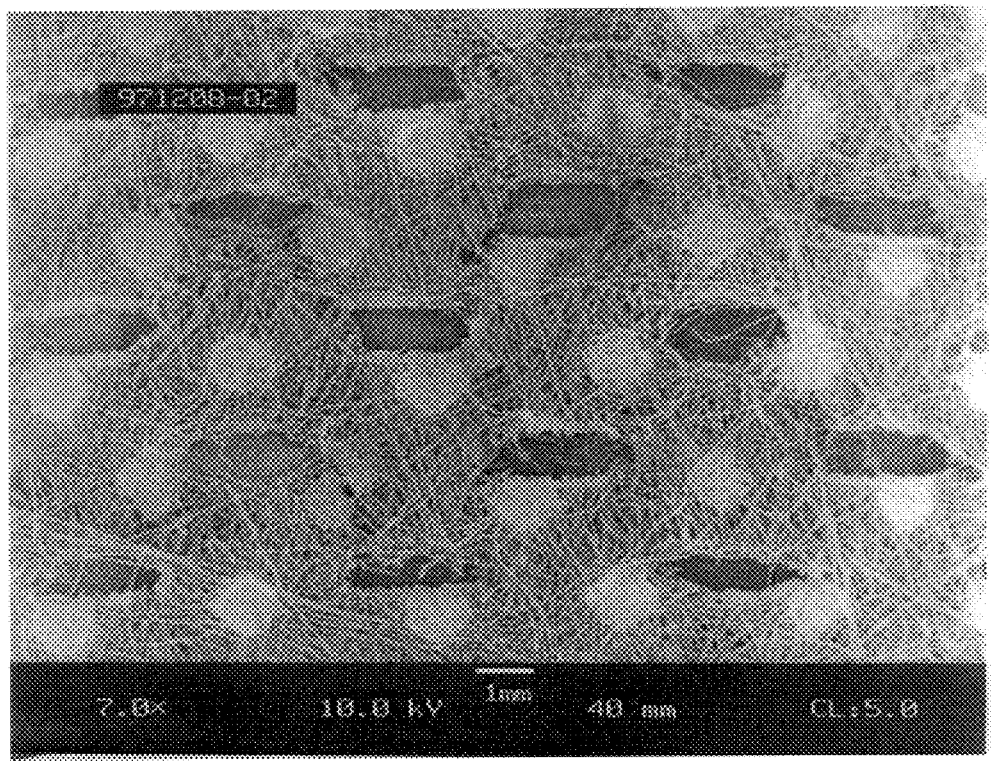
FIG. 3 is photomicrograph of a bonded and apertured nonwoven prepared in accordance with the invention and comprising continuous spunbond bicomponent filaments having a sheath of 100% polyethylene and a core of 100% polypropylene in a sheath to core ratio by weight of 1:1.

A photomicrograph of the apertured web of Example 1 is shown in FIG. 3. As can be from the photomicrograph, the aperturing process produces a region of fused or partially melted polyethylene present along the peripheral portions of the apertures. These regions are bonded to the fibers of the web to preserve the coherent and extensible structure of the web. These regions of polyethylene along the peripheral portions of the apertures remain soft and are not hard as is typical of prior art polypropylene webs. The apertures are of well-defined clarity and have retained a substantial portion of the elongate shape and aspect ratio of the frangible bond sites. The non-frangible bond sites have remained intact and the web exhibits low fuzz with few broken filaments extended over the apertures, which preserves good fluid strike-through capability.

The physical properties of the web were evaluated and are tabulated, along with that of several additional examples, in Table 1, below, labeled as Sample No. 1. For this example, the web uniformity was acceptable. Cross-direction strip tensile was evaluated at 1,273 g, which is many times higher than that for any of the comparison examples. Cross direction total energy absorbed ("TEA"), was 174.3 gcm/cm$^2$, which is a measure of the area under the cross-direction strip tensile curve and indicates that the web had a high toughness, well beyond any of the comparison webs that were tested, for withstanding the aperturing process and for serving as a topsheet in diapers, wipes, and the like disposable absorbent nonwovens. Machine direction strip tensile and TEA were also high at 2290 g and 396.4 gcm/cm$^2$.

EXAMPLE 2

A nonwoven web of continuous spunbond bicomponent filaments was produced using the same components, at the same basis weight, and in the same manner as that used in Example 1, except that the concentric sheath and core bicomponent filaments used to form the web were prepared with filaments having a ratio of 9:1 of polyethylene in the sheath to polypropylene in the core. The bonding pattern and conditions were the same both for the frangible and non-frangible bonds.

Figure 4:
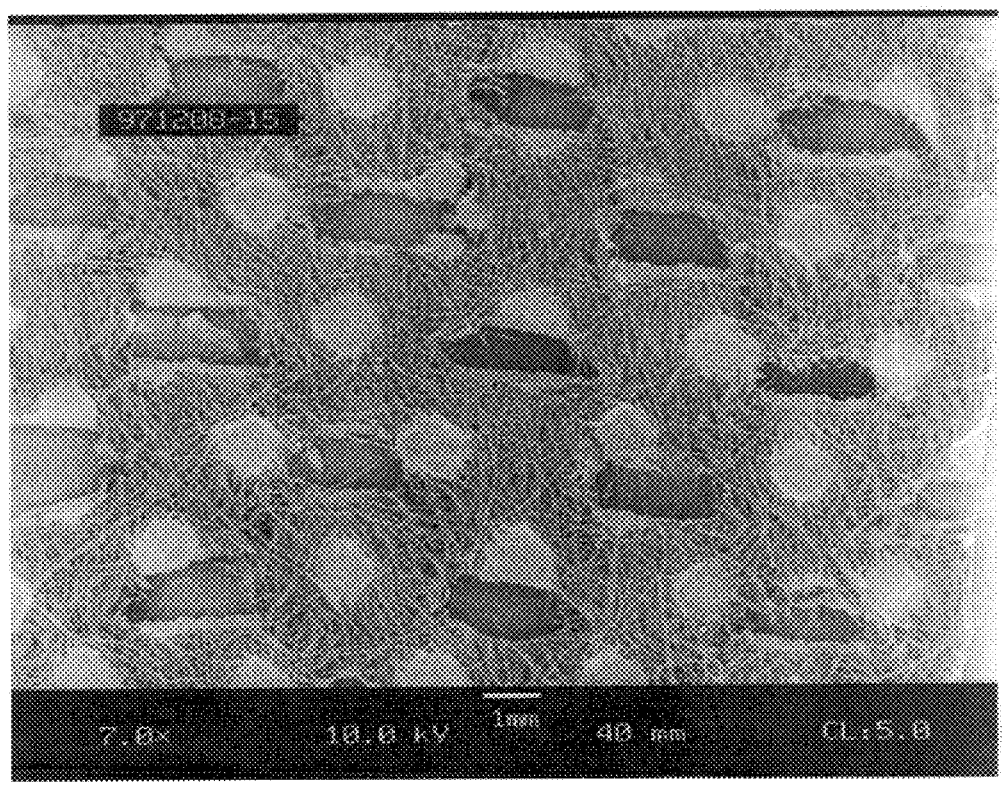
FIG. 4 is a photomicrograph of a bonded and apertured nonwoven prepared in accordance with the invention and comprising continuous spunbond bicomponent filaments having a sheath of 100% polyethylene and a core of 100% polypropylene in a sheath to core ratio by weight of 9:1.

A photomicrograph of the apertured nonwoven web that was produced in accordance with Example 2 is shown in FIG. 4. The additional polyethylene in the sheath produced somewhat more pronounced regions of fused polyethylene present along the peripheral portions of the apertures as compared to the web of Example 1 that is shown in FIG. 3. The aperture clarity is high with few broken filaments extending into the apertures and the web is a low fuzz web, which is desirable for rapid fluid strike-through. The aspect ratio and elongate appearance of the frangible bond sites is substantially preserved in the apertures shown in FIG. 4.

The physical properties of the web were evaluated and are tabulated below in Table 1, labeled as Sample No. 5. For this example, the web uniformity was acceptable and of somewhat better quality than that of Sample No. 1. Cross-direction strip tensile was evaluated at 636 g, which is several times higher than that for any of the comparison examples. Cross direction total energy absorbed ("TEA"), was 68.03 gcm/cm$^2$, which, while less than that for Sample No. 1, which had less polyethylene in the filament, nevertheless indicates that the web had a high toughness, well beyond any of the comparison webs that were tested, for withstanding the aperturing process and for serving as a topsheet in diapers, wipes, and the like disposable absorbent nonwovens. Machine direction strip tensile and TEA were also high at 1063 g and 149.06 gcm/cm$^2$.

EXAMPLE 3

Example 3 is a comparative example of an apertured nonwoven web produced in accordance with the prior art and shown in FIG. 3. Example 3 is of a typical apertured nonwoven fabric that has been produced at the same basis weight and in a similar manner to that set forth in Examples 1 and 2, except for the use of monocomponent filaments in which the fiber spinning polymer is 100 percent polypropylene, the same polypropylene used as the core for the bicomponent filaments of Examples 1 and 2. The web was bonded to produce frangible and non-frangible bond sites in the same manner as recited in Example 1.

Figure 5:
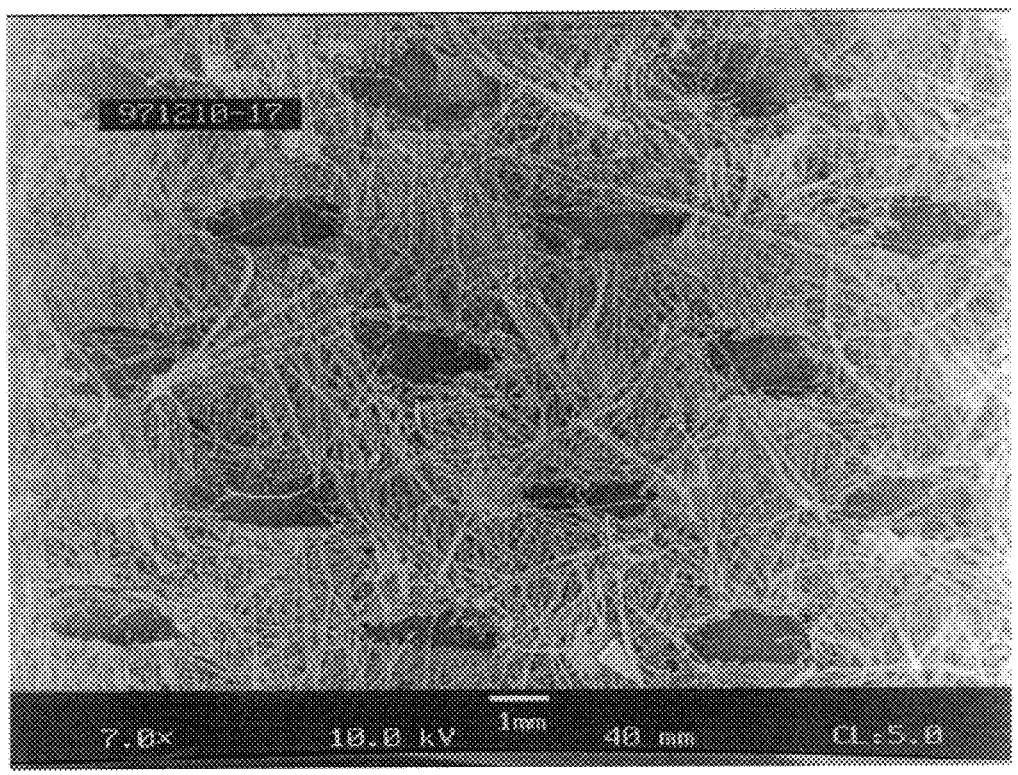
FIG. 5 is photomicrograph of a bonded and apertured nonwoven web of the prior art comprising continuous spunbond monocomponent filaments of 100% polypropylene.

As can be seen in FIG. 5, the apertures of the apertured web made with polypropylene continuous spunbond homofilaments are non-uniform and somewhat irregular in shape. The shape and overall aspect, ratio of the frangible bond sites has not been retained to the same degree as can be observed in the webs of the invention of FIGS. 3 and 4. A number of broken ends of filaments appear to extend from the fabric and across the apertures, which increases undesirable fuzz in the fabric as compared to the nonwoven webs of the invention and tends to reduce strikethrough values. No pronounced zones of fused polymer can be observed that are present along peripheral portions of the apertures to bond to the fibers to lend coherence to the extensible nonwoven web. The non-frangible bond sites, although present, are not as clear and well defined as those seen in FIGS. 3 and 4.

The physical properties of the web were evaluated and are tabulated below in Table 1, labeled as comparative Sample No. C1, where the C stands for "comparative." For this Example C1, the web uniformity was good, but the apertures were rated extremely poor and the web was fuzzy. Cross-direction strip tensile was evaluated at 233 g, which is several times lower than that for any of the multicomponent polymer examples. Cross direction total energy absorbed ("TEA"), was 22.88 gcm/cm$^2$, which is significantly lower than that for any of the multicomponent polymer examples and indicates that the web is unlikely to have the favorable processing characteristics of the examples of the invention. Machine direction strip tensile and TEA were also relatively low at 929 g and 59.95 gcm/cm$^2$.

Table 1, below, shows data for additional examples further demonstrating the superior characteristics of the apertured nonwoven webs of the invention, including spunbond webs prepared from bicomponent continuous filaments having a polyethylene sheath and cores selected from nylon-6 (Sample 2 and 6), polybutylene terephthalate (Sample 3), and polyethylene terephthalate (Sample 3). Comparative examples are included of nonwoven webs prepared from continuous monocomponent filaments selected from polyethylene (Sample C2), nylon-6 (Sample C3), and polyethylene terephthalate (Sample c4). All of the examples of the invention produced webs of remarkable toughness compared to the prior art, and having the softness of the polyethylene sheath. Almost all the webs of the invention had better aperture clarity and web uniformity.

TABLE 1

| Sample ID | Description | Aperture Rating | CD Strip Tensile (g) | MD Strip Tensile (g) | Fuzzy | CD TEA (gcm/cm$^2$) | MD TEA (gcm/cm$^2$) |
| --- | --- | --- | --- | --- | --- | --- | --- |
| C1 | 100% PP | 5.2 | 233 | 929 | Yes | 22.88 | 59.95 |
| C2 | 100% PE | 2.6 | 249 | 352 | Yes | 28.80 | 43.7 |
| C3 | 100% PA-6 | 6 | 287 | 957 | Yes | 23.69 | 60.16 |
| C4 | 100% PET | 5.6 | 54 | 279 | Yes | 4.30 | 10.53 |
| 1 | 50% PE/50% PP | 1.6 | 1273 | 2290 | No | 174.30 | 396.4 |
| 2 | 50% PE/50% PA-6 | 3.6 | 1947 | 3541 | No | 230.5 | 511.7 |
| 3 | 50% PE/50% PBT | 1 | 1090 | 1705 | No | 122.9 | 258.8 |
| 4 | 50% PE/50% PET | 1 | 1350 | 2823 | No | 115.80 | 470.2 |
| 5 | 90% PE/10% PP | 1.2 | 636 | 1063 | No | 68.03 | 149.6 |
| 6 | 90% PE/10% PA-6 | 1.4 | 1070 | 2123 | No | 152.1 | 210.2 |

Aperture Rating Definition:
1 - Good Apertures and Good Uniformity.
2 - Good Apertures and Poor Uniformity.
3 - Poor Apertures and Good Uniformity.
4 - Poor Apertures and Poor Uniformity.
5 - Extremely Poor Apertures and Good Uniformity.
6 - Extremely Poor Apertures and Poor Uniformity.

Strip tensile strength, peak elongation and TEA were evaluated by breaking a one inch by seven inch long sample generally following ASTM D1682-64, the one-inch cut strip test. The instrument cross-head speed was set at 5 inches per minute and the gauge length was set at 5 inches. The strip tensile strength, reported as grams per centimeter, is generally the average of at least 8 measurements. Peak elongation is the percent increase in length noted at maximum tensile strength. Total tensile energy absorption (TEA) is calculated from the area under the stress-strain curve generated during the strip tensile test.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A nonwoven web comprising a plurality of multicomponent fibers, said fibers comprising at least two thermoplastic polymer components arranged in at least first and second separate continuous structured domains, said polymer component of said first domain comprising polyethylene, and a plurality of discrete, spaced-apart, frangible bond sites of fused polymer bonding said fibers to form a coherent extensible nonwoven web, said frangible bond sites being structured and arranged to readily rupture when subjected to tensile stress to form discrete, spaced-apart apertures in the nonwoven fabric, and said web having a peak elongation of at least 200 percent.

2. A nonwoven web comprising a plurality of multicomponent fibers, said fibers comprising at least two thermoplastic polymer components arranged in at least first and second separate continuous structured domains, said polymer component of said first domain comprising polyethylene, and a plurality of discrete, spaced-apart, frangible bond sites of fused polymer bonding said fibers to form a coherent extensible nonwoven web, said frangible bond sites being structured and arranged to readily rupture when subjected to tensile stress to form discrete, spaced-apart apertures in the nonwoven fabric, and said web having a peak elongation of at least 100 percent, and wherein the web has a minimum cross-machine direction tensile strength of 300 g.

3. The nonwoven web of claim 1 wherein said polymer component of said second domain is a member selected from the group consisting of polypropylene, polyamide, and polyester.

4. The nonwoven web of claim 1 wherein said frangible bond sites are elongated in shape and have an aspect ratio of at least 3:1.

5. The nonwoven web of claim 4 wherein said frangible bond sites have an aspect ratio of at least 4:1.

6. The nonwoven web of claim 1 wherein said first domain comprises from about 20% to about 90% by weight of the fiber.

7. The nonwoven web of claim 1 wherein said multicomponent fibers are selected from the group consisting of multicomponent spunbond continuous filaments, multicomponent carded staple fibers, and multicomponent meltblown fibers.

8. The nonwoven web of claim 1 wherein said multicomponent fibers are continuous spunbond bicomponent filaments having the polymer components arranged in sheath-core structured domains, wherein said sheath domain is said first domain and said core domain is said second domain.

9. The nonwoven web of claim 1 wherein said first domain is formed entirely of polyethylene and said second domain comprises polypropylene.

10. A nonwoven web comprising a plurality of multicomponent fibers, said fibers comprising at least two thermoplastic polymer components arranged in at least first and second separate continuous structured domains, said polymer component of said first domain comprising polyethylene, and a plurality of discrete, spaced-apart, frangible bond sites of fused polymer bonding said fibers to form a coherent extensible nonwoven web, said frangible bond sites being structured and arranged to readily rupture when subjected to tensile stress to form discrete, spaced-apart apertures in the nonwoven fabric, and said web having a peak elongation of at least 100 percent, wherein at least one of said first and second domains comprises a multipolymer blend of at least two different polymers, and wherein said first domain comprises a multipolymer blend of polyethylene with at least one additional polymer, said polymers being present as a lower-melting dominant continuous polyethylene phase and at least one higher-melting noncontinuous phase dispersed therein, said lower melting continuous phase forming at least 20% by weight of the polymer blend.

11. The nonwoven web of claim 10, wherein said at least one additional polymer comprises polypropylene.

12. The nonwoven web of claim 10 wherein said second domain comprises a multipolymer blend of at least two different polymers, said polymers being present as a higher-melting dominant continuous phase and at least one lower-melting noncontinuous phase dispersed therein, said higher melting continuous phase comprising a propylene polymer and said at least one lower-melting noncontinuous phase comprising a polyethylene polymer.

13. The nonwoven web of claim 1 additionally including a plurality of discrete, spaced-apart, non-frangible bond sites bonding said fibers, said non-frangible bond sites being structured and arranged to maintain their integrity when subjected to tensile stress to impart strength and integrity to the web.

14. The nonwoven web of claim 13 wherein said non-frangible bond sites are have an aspect ratio of no more than 2:1.

15. A nonwoven web comprising a plurality of bicomponent fibers, said fibers comprising first and second polymer components arranged in first and second separate continuous structured domains, said polymer component of said first domain comprising polyethylene, and said polymer component of said second domain being selected from the group consisting of polypropylene, polyester and polyamide, and a plurality of discrete, spaced-apart, frangible bond sites of fused polymer bonding said fibers to form a coherent extensible nonwoven web, said frangible bond sites having an aspect ratio of at least 3:1 and being structured and arranged to readily rupture when subjected to tensile stress to form discrete, spaced-apart apertures in the nonwoven fabric, and said web having a peak elongation of at least 100 percent, and wherein the web has a minimum cross-machine direction tensile strength of 300 g.

16. A nonwoven web comprising a plurality of multicomponent fibers, said fibers comprising at least two thermoplastic polymer components arranged in at least first and second separate continuous structured domains, said polymer component of said first domain comprising polyethylene, and said polymer component of said second domain having a higher modulus than that of said polymer component of said first domain, a first plurality of discrete, spaced-apart, frangible bond sites of fused polymer bonding said fibers to form a coherent extensible nonwoven webs said frangible bond sites being structured and arranged to readily rupture when subjected to tensile stress to form discrete, spaced-apart apertures in the nonwoven fabric, and a second plurality of discrete, spaced-apart, non-frangible bond sites bonding said fibers, said non-frangible bond sites being structured and arranged to maintain their integrity when subjected to tensile stress to impart strength and integrity to the web, and said web having a peak elongation of at least 100 percent, and wherein the web has a minimum cross-machine direction tensile strength of 300 g.

17. A nonwoven web comprising a plurality of bicomponent fibers, said fibers comprising first and second polymer components arranged in first and second separate continuous structured domains, said polymer component of said first domain comprising polyethylene, and said polymer component of said second domain being selected from the group consisting of polypropylene, polyester and polyamide, a first plurality of discrete, spaced-apart, frangible bond sites of fused polymer bonding said fibers to form a coherent extensible nonwoven web, said frangible bond sites having an aspect ratio of at least 3:1 and being structured and arranged to readily rupture when subjected to tensile stress to form discrete, spaced-apart apertures in the nonwoven fabric, and a second plurality of discrete, spaced-apart, non-frangible bond sites bonding said fibers, said non-frangible bond sites having an aspect ratio of no more than 2:1 and being structured and arranged to maintain their integrity when subjected to tensile stress to impart strength and integrity to the web, and said web having a peak elongation of at least 100 percent, and wherein the web has a minimum cross-machine direction tensile strength of 300 g.

18. An apertured nonwoven web comprising a plurality of multicomponent fibers, said fibers comprising at least two thermoplastic polymer components arranged in at least first and second separate continuous structured domains, said polymer component of said first domain comprising polyethylene, a plurality of discrete, spaced-apart, apertures formed in said web, and a region of fused polyethylene present along peripheral portions of at least some of said apertures, said fused polyethylene bonding said fibers to form a coherent extensible nonwoven web, and wherein the web has a total energy absorption in at least one of the machine direction or the cross-machine direction of at least 50 gcm/cm$^2$.

19. The nonwoven web of claim 18 wherein the web has a total energy absorption is greater than 100 gcm/cm$^2$.

20. An apertured nonwoven web comprising a plurality of multicomponent fibers, said fibers comprising at least two thermoplastic polymer components arranged in at least first and second separate continuous structured domains, said polymer component of said first domain comprising polyethylene, a plurality of discrete, spaced-apart, apertures formed in said web, and a region of fused polyethylene present along peripheral portions of at least some of said apertures, said fused polyethylene bonding said fibers to form a coherent extensible nonwoven web, and wherein the web has a strip tensile strength in at least one of the machine direction or the cross-machine direction of at least 300 g.

21. The nonwoven web of claim 18 wherein said first domain comprises from about 20% to about 90% by weight of the fiber.

22. The nonwoven web of claim 18 wherein said first domain is formed entirely of polyethylene and said second domain comprises polypropylene.

23. An apertured nonwoven web comprising a plurality of multicomponent fibers, said fibers comprising at least two thermoplastic polymer components arranged in at least first and second separate continuous structured domains, said polymer component of said first domain comprising polyethylene, a plurality of discrete, spaced-apart, apertures formed in said web, and a region of fused polyethylene present along peripheral portions of at least some of said apertures, said fused polyethylene bonding said fibers to form a coherent extensible nonwoven web, and wherein at least one of said first and second domains comprises a multipolymer blend of at least two different polymers.

24. An apertured nonwoven web comprising a plurality of multicomponent fibers, said fibers comprising at least two thermoplastic polymer components arranged in at least first and second separate continuous structured domains, said polymer component of said first domain comprising polyethylene, a plurality of discrete, spaced-apart, apertures formed in said web, and a region of fused polyethylene present along peripheral portions of at least some of said apertures, said fused polyethylene bonding said fibers to form a coherent extensible nonwoven web, and wherein said plurality of multicomponent fibers include a first plurality of fibers in which said polymer component of said first domain comprises from about 40% to about 60% by weight of the fiber and a second plurality of fibers in which said polymer component of said first domain comprises from about 70% to about 90% by weight of the fiber.

25. An apertured nonwoven web comprising a plurality of multicomponent fibers, said fibers comprising at least two thermoplastic polymer components arranged in at least first and second separate continuous structured domains, said polymer component of said first domain comprising polyethylene, a plurality of discrete, spaced-apart, apertures formed in said web, and a plurality of discrete, spaced-apart point bond sites present at locations between said apertures, said bond sites bonding said fibers to impart strength and integrity to the web, and wherein the web has a minimum cross-machine direction tensile strength of 300 g.

26. The nonwoven web of claim 25 wherein said point bond sites have an aspect ratio of no more than 2:1.

27. The nonwoven web of claim 25 including a region of fused polyethylene present along peripheral portions of at least some of said apertures.

28. The nonwoven web of claim 25 wherein the multicomponent fibers are selected from the group consisting of the following polymer combinations: polyethylene/polypropylene, polyethylene/polyethylene terephthalate, polyethylene/polybutylene terephthalate, and polyethylene/nylon-6 wherein the components are arranged in a configuration of a side-by-side filament, a sheath/core filament in which the sheath is polyethylene, a multi-segmented pie, or hollow filaments of these configurations.

29. An apertured nonwoven web comprising a plurality of bicomponent spunbond filaments, said filaments having a sheath comprised of polyethylene and a core comprised of polypropylene, and wherein the sheath constitutes 20 to 90 percent by weight of the filaments, a plurality of discrete, spaced-apart, apertures formed in said web, a region of fused polyethylene present along peripheral portions of said apertures, said fused polyethylene bonding said fibers to form a coherent extensible nonwoven web, and a plurality of discrete, spaced-apart point bond sites present at locations between said apertures, said bond sites bonding said fibers to impart strength and integrity to the web, wherein the web has a total energy absorption in at least one of the machine direction or the cross-machine direction of at least 50 gcm/cm$^2$.

30. The nonwoven web of claim 29 wherein the total energy absorption in at least one of the machine direction or the cross-machine direction is greater than 100 gcm/cm$^2$.

31. The nonwoven web of claim 29 wherein the total energy absorption in both the machine direction and the cross-machine direction is greater than 100 gcm/cm$^2$.

32. An apertured nonwoven web comprising a plurality of bicomponent spunbond filaments, said filaments having a sheath comprised of polyethylene and a core comprised of polypropylene, and wherein the sheath constitutes 20 to 90 percent by weight of the filaments, a plurality of discrete, spaced-apart, apertures formed in said web, a region of fused polyethylene present along peripheral portions of said apertures, said fused polyethylene bonding said fibers to form a coherent extensible nonwoven web, and a plurality of discrete, spaced-apart point bond sites present at locations between said apertures, said bond sites bonding said fibers to impart strength and integrity to the web, and wherein said plurality of bicomponent fibers include a first plurality of fibers in which said polymer component of said first domain comprises from about 40% to about 60% by weight of the fiber and a second plurality of fibers in which said polymer component of said first domain comprises from about 70% to about 90% by weight of the fiber.

33. An apertured nonwoven web comprising a plurality of bicomponent spunbond filaments, said filaments having a sheath comprised of polyethylene and a core comprised of polypropylene, and wherein the sheath constitutes 20 to 90 percent by weight of the filaments, a plurality of discrete, spaced-apart, apertures formed in said web, a region of fused polyethylene present along peripheral portions of said apertures, said fused polyethylene bonding said fibers to form a coherent extensible nonwoven web, and a plurality of discrete, spaced-apart point bond sites present at locations between said apertures, said bond sites bonding said fibers to impart strength and integrity to the web, and including a surfactant on said fibers.

34. An apertured nonwoven web comprising a plurality of bicomponent spunbond filaments formed of at least two thermoplastic polymer components arranged in first and second separate continuous structured domains, said filaments being disposed in first and second groups of differing composition, said first domain in said first group of filaments comprising from about 40% to about 60% by weight of the filament, and said first domain in said second group of filaments comprising from about 70% to about 90% by weight of the filament, a first plurality of discrete, spaced-apart point bond sites bonding the filaments of said first group, a second plurality of discrete, spaced-apart point bond sites bonding the filaments of said second group, and a plurality of discrete, spaced-apart, apertures formed in said web, and wherein regions of fused polymer are present along peripheral portions of the apertures which bond together the filaments of said first and second groups to form a unitary composite apertured web, and wherein said polymer component of said first domain comprises polyethylene.

35. The nonwoven web of claim 34 wherein said filaments have a sheath comprised of polyethylene and a core comprised of polypropylene.

36. A topsheet for a disposable absorbent article comprising the apertured nonwoven web of claim 18.

37. A disposable wipe comprising the apertured nonwoven web of claim 18.

38. The nonwoven web of claim 2 wherein said polymer component of said second domain is a member selected from the group consisting of polypropylene, polyamide, and polyester.

39. The nonwoven web of claim 2 wherein said frangible bond sites are elongated in shape and have an aspect ratio of at least 3:1.

40. The nonwoven web of claim 39 wherein said frangible bond sites have an aspect ratio of at least 4:1.

41. The nonwoven web of claim 2 wherein said first domain comprises from about 20% to about 90% by weight of the fiber.

42. The nonwoven web of claim 2 wherein said multicomponent fibers are selected from the group consisting of multicomponent spunbond continuous filaments, multicomponent carded staple fibers, and multicomponent meltblown fibers.

43. The nonwoven web of claim 2 wherein said multicomponent fibers are continuous spunbond bicomponent filaments having the polymer components arranged in sheath-core structured domains, wherein said sheath domain is said first domain and said core domain is said second domain.

44. The nonwoven web of claim 2 wherein said first domain is formed entirely of polyethylene and said second domain comprises polypropylene.

45. An apertured nonwoven web comprising a plurality of bicomponent spunbond filaments formed of at least two thermoplastic polymer components arranged in first and second separate continuous structured domains, said filaments being disposed in first and second groups, a first plurality of discrete, spaced-apart point bond sites bonding the filaments of said first group, a second plurality of discrete, spaced-apart point bond sites bonding the filaments of said second group, and a plurality of discrete, spaced-apart, apertures formed in said web, wherein regions of fused polymer are present along peripheral portions of the apertures which bond together the filaments of said first and second groups to form a unitary composite apertured web, and wherein said polymer component of said first domain comprises polyethylene.

* * * * *

UNITED STATES PATENT AND TRADEMARK OFFICE
CERTIFICATE OF CORRECTION

PATENT NO. : 6,632,504 B1 Page 1 of 1
DATED : October 14, 2003
INVENTOR(S) : Gillespie et al.

It is certified that error appears in the above-identified patent and that said Letters Patent is hereby corrected as shown below:

<u>Title page,</u>
Item [56], References Cited, U.S. PATENT DOCUMENTS, insert the following:

-- 5,718,972    2/1998    Murase et al.
        6,169,045    1/2001    Pike et al. --.

<u>Column 16,</u>
Line 4, "webs" should read -- web, --;
Lines 48-49, cancel "web has a".

Signed and Sealed this

Tenth Day of February, 2004

JON W. DUDAS
*Acting Director of the United States Patent and Trademark Office*